United States Patent [19]

Umeda et al.

[11] 4,431,790
[45] Feb. 14, 1984

[54] CURING AGENTS FOR POLYURETHANE AND PROCESS USING SAME

[75] Inventors: Arihiko Umeda, Tokyo; Seiichi Ota, Ichikawa; Yoshiyuki Iwase, Tokyo, all of Japan

[73] Assignee: Texaco Inc., White Plains, N.Y.

[21] Appl. No.: 289,689

[22] Filed: Aug. 3, 1981

[30] Foreign Application Priority Data

Aug. 12, 1980 [JP] Japan .................................. 55-109806

[51] Int. Cl.³ ...................... C08G 18/32; C08G 18/62; C09K 3/00
[52] U.S. Cl. ...................................... 528/73; 252/182; 252/188.31; 528/75; 528/77; 560/169
[58] Field of Search .......................... 528/73, 77, 75; 252/188.3 R, 182; 560/169

[56] References Cited

U.S. PATENT DOCUMENTS

| | | | |
|---|---|---|---|
| 4,272,619 | 6/1981 | Balle et al. | 528/75 |
| 4,286,074 | 8/1981 | Davis et al. | 528/75 |
| 4,296,212 | 10/1981 | Ewen et al. | 528/75 |

FOREIGN PATENT DOCUMENTS

| | | |
|---|---|---|
| 1917408 | 11/1969 | Fed. Rep. of Germany . |
| 1966058 | 6/1971 | Fed. Rep. of Germany . |
| 1266561 | 3/1972 | United Kingdom . |

*Primary Examiner*—H. S. Cockeram
*Attorney, Agent, or Firm*—Carl G. Ries; Robert A. Kulason; Henry W. Archer

[57] ABSTRACT

Disclosed are novel curing agents for polyurethanes comprising reaction products of (1) a polyoxy alkylenepolyamine with (2) an alpha-substituted acrylic acid derivative wherein the substituent has a terminal hydroxyl group or (3) with a compound having an oxyrane ring and reaction products of (1) and (2) above, with (3) and (1) and (3) above, with (2). Also disclosed is a process for making polyurethanes by condensing a polyol with an isocyanate in the presence of the present curing agents in an amount ranging from 5 to 100 percent by weight of the polyol.

17 Claims, No Drawings

CURING AGENTS FOR POLYURETHANE AND PROCESS USING SAME

FIELD OF THE INVENTION

This invention relates to novel curing agents having improved reactivity toward isocyanates and suitable gel time and to a process for making polyurethane using such agents without any accelerators.

DESCRIPTION OF PRIOR DISCLOSURES

It is already known that polyoxyalkylenepolyamines can be used as curing agents when polyurethanes are manufactured from a polyisocyanate and a polyol (e.g. Official Bulletin Patent Publication Sho. 49-28914). However, polyoxyalkylenepolyamines are unsatisfactory as a curing agent because of their extremely high reactivity with isocyanates.

Although a method for lowering the reactivity of the amine with isocyanates by adding thereto a cyanoalkyl group or a alkyleneoxide group was proposed in Official Bulletin Patent Publication Sho. 49-28914 and U.S. Pat. No. 4,075,130, the resulting products had insufficient solubility in polyols.

The literature on the Michael-type addition reaction feature of this invention includes:

Naoya Ogata, Tomohiko Asahara, Bull Chem. Soc. Jpn, 39, 1486-1490 (66);

Kohei Sanui, Naoya Ogata, Bull Chem. Soc. Jpn, 1727 (67); and

Naoya Ogata, Highpolymer Chemistry, 27, 1-19 (70).

As will be seen hereinafter none of these disclose in any manner Applicants' novel curing agents and process for using same.

SUMMARY OF THE INVENTION

The present invention provides curing agents for making polyurethanes comprising reaction products of: (1) a polyoxyalkylenepolyamine with (2) an alpha-substituted acrylic acid derivative wherein the substituent has a terminal hydroxyl group; or (3) a compound having an oxyrane ring and reaction products of (1) and (2), above, with (3) and reaction products of (1) and (3), above, with (2).

The invention also provides a process for making polyurethanes without using any accelerator which comprises adding to a polyol 5 to 100 percent by weight of at least of the above curing agents; condensing with an isocyanate and recovering the product so formed.

DESCRIPTION OF BEST MODE OF PRACTICING THE INVENTION

The polyoxyalkylenepolyamines used in this invention include:

polyoxypropylenediamines of the formula $$H_2NCH(CH_3)CH_2[OCH_2CH(CH_3)]_nNH \quad (I)$$

wherein n=2-50 bispropylenediamines of polyoxyethylenes of the formula $$H_2N(CH_2)_3[O(CH_2)_2]_mO(CH_2)_3NH_2 \quad (II)$$

wherein m=1-50 and
triamines of polyoxypropylenes of the formula

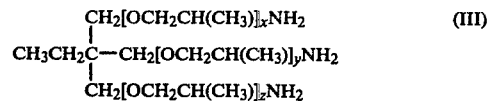

wherein x+y+x=3-10

The polyoxyalkylenepolyamine of formulas (I) and (III) is preferred. The preferred compound of formula (I) has n=2.6, n=5.6 and n=33.1. The preferred compounds of formulas (II) and (III) are those where n=2 and x+y+z=5.3, respectively.

The alpha-substituted acrylic acid derivatives with a substituent group having a terminal hydroxyl group that are used in this invention, are acrylic acid derivatives, methacrylic acid derivatives and alpha-cyanoacrylic acid derivatives, characterized by formula (IV):

wherein

X=H, —CH$_3$, —CN; Y=hydroxyalkylene, hydroxyalkyleneoxide, N-substituted hydroxyalkylene, N-substituted hydroxyalkyleneoxide and hydroxyalkyleneiminoalkylene (except the hydroxycarbonyl group).

Exemplary alpha-substituted acrylic acid derivatives include acrylate, methacrylate, alphacyanoacrylate, N-substituted acrylamide, N-substituted methacrylamide, N-substituted a-cyanoacrylamide (each includes N,N-bis substituted) of hydroxyethyl, hydroxypropyl, hydroxybutyl, polyoxyethyleneglycol, polyoxypropyleneglycol and hydroxyethyliminoethyl derivatives of acrylic acid.

Of these, the preferred compounds for use in this invention are hydroxyethylacrylate, hydroxyethylmethacrylate, hydroxyethylcyanoacrylate and diethyleneglycolmonoacrylate.

The reaction between the polyoxyalkelenepolyamine and the acrylate produces a Michael-type reaction adduct as shown by I.R. absorbance. This reaction can be carried out with a solvent such as an alcohol (butanol), ether (dioxane), an aromatic (toluene, oxylene) or alphiatic hydrocarbon in an amount equal to 10-80% of the charge reaction as required.

The mixture may be heated as required. The Michael adduct of the polyoxyalkylenepolyamine and the alpha-substituted acrylic acid derivative is produced almost quantitatively. Even if a small quantity of unreacted compounds is contained, it does not adversely affect polyurethane curing. Preferably the unreacted material content should not exceed 1% of the curing agent.

The reaction temperature is less than 200° C. and the stirring time is approx. 48 hours. Where an alphacyanoacrylic acid derivative is used as the alpha-substituted acrylic acid derivative, it sometimes generates heat and therefore, cooling is necessary in such case. The molar ratio of polyoxyalkylenepolyamine and alpha-substituted acrylic acid derivative used is in the range of 5:1 to 1:5, preferably 3:1 to 1:3.

The reaction between polyoxyalkylenepolyamines and oxyrane compounds proceeds as follows:

$$H_2N-R-NH_2 + R'CH\underset{O}{-\!\!-\!\!-}CH_2 \longrightarrow$$

$$\underset{\underset{OH}{|}}{R'CHCH_2HN}-R-\underset{\underset{OH}{|}}{NHCH_2CHR'}$$
$$+$$
$$(HOCHR'CH_2)_2N-R-\underset{\underset{OH}{|}}{NHCH_2CHR'}$$

wherein

R = polyoxyalkylene
R' = H, alkyl group, aromatic group, oxyalkyl group, and oxyalkylaromatic group Suitable epoxy compounds include ethyleneoxide, propyleneoxide, n-butylglycidyl ether and styreneoxide.

The parameters for the reaction of polyamine with epoxy compounds are as follows:

| (a) | Reactants, molar ratios; | polyamine (diamine type)/epoxy = 1/1.5 to 1:3.8 mol ratio (optimum range: ] to 1:3.5 mol ratio) polyamine (triamine type)/epoxy = 1:2 to 1:5.5 mol ratio (optimum range: ⅓ to 1:4.5 mol ratio) |
|---|---|---|
| (b) | Reaction temperature | room temp. - 200° C. (optimum range 60–150°C.) |
| (c) | Reaction time | 30 minutes - 48 hours (optimum range 1–20 hours) |

The reaction between (polyamine+epoxy compound)+acrylate proceeds as follows:

$$HOCHR'CH_2HN-R-NHCH_2CHR'OH + CH_2{=}\underset{\underset{O}{\|}}{C}{-}\underset{X}{\overset{|}{C}}{-}Y$$

$$(HOCHR'CH_2)_2N-R-NHCH_2CHR'OH$$

$$\underset{YOCCHXCH_2}{HOCHR'CH_2}\!\!\searrow\!\!N-R-N\!\!\swarrow\!\!\underset{CH_2CXHCOY}{CH_2CHR'OH}$$

$$+$$

$$(HOCHR'CH_2)_2N-R-N\!\!\swarrow\!\!\underset{CH_2CXHCOY}{CH_2CHR'OH}$$

R=polyoxyalkylene, R', X and Y are as above.
The reaction parameters for above reaction are as follows:

| (a) | Reactants, molar ratio | polyamine epoxy compound/acrylate = 1/1 to 1:4 mol ratio (optimum range ] to 1:3.5 mol ratio) |
|---|---|---|
| (b) | Reaction temperature | room temp to 200° C. (optimum range: 60° C. to 150° C.) |
| (c) | Reaction time | 1 to 48 hours (optimum range: 3 to 20 hours) |

The reaction parameters for the reaction between the polyamine, acrylate and epoxy reactants are substantially as above indicated for the polyamine, epoxy and acrylate reactants.

The invention is illustrated in non limiting fashion by the following examples. The "reference" examples show the use of the various curing agents in making polyurethane.

EXAMPLES 1–3

One mol of each polyoxypropylenediamine having the molecular weight shown in Table 1 was put in a 3-liter roundbottom flask. Then, 2 mols of hydroxyethylacrylate ester was added slowly, while stirring at temperature of 100° C. After the addition, the mixture was further stirred for 10 hours, so that a Michael addition reaction took place. The yield of adduct of polyoxypropylenediamine and hydroxyethylacrylate in each reaction product is shown in Table 1 and is nearly quantitative.

TABLE 1

| Examples | Molecular weight of polyoxypropylenediamine | Yield of Michael Adduct |
|---|---|---|
| 1 | 230 | 98% |
| 2 | 400 | 98% |
| 3 | 2000 | 95% |

EXAMPLE 4

Except for the use of one mol of polyoxypropylenetriamine (400 g) having molecular weight 400 in lieu of one mol (230 g) of polyoxypropylenediamine having molecular weight of 230, and 3 mols (348 g) of hydroxyethylacrylate, the procedure of Example 1 was repeated. The yield of adduct of polyoxypropylenetriamine and hydroxyethylacrylate was 98%.

REFERENCE EXAMPLES 1–4

0.023 mol of the compounds of Ex. 1–4 was put in a 500-ml roundbottom flask. Then, 0.05 mole of polypropyleneglycol having a molecular weight of 2,000 was added with 0.1 mol of tolylenediisocyanate. This mixture was stirred and blended at room temperature. The time required until gel of the mixture was measured as an indicator of reactivity with isocyanate. The results are shown in Table 2.

Except for using 0.023 mol of polyoxypropylenediamine having molecular weight of 230 instead of 0.023 mol of compound shown in Example 1 of for comparison, the procedure was repeated, measuring the gel time.

TABLE 2

| Reference Examples | Curing Agent Compound | Gel time (minute) |
|---|---|---|
| 1 | Example 1 | 15 |
| 2 | Example 2 | 22 |
| 3 | Example 3 | 28 |
| 4 | Example 4 | 20 |
| Control 1 | Polyoxypropylenediamine (MW 230) | 8 seconds |

EXAMPLE 5

One mole of polyoxypropylenediamine having molecular weight shown in Table 3 was put in a 3-liter round-bottom flask. Then, 2 mols (260 g) of hydroxyethylmethacrylate was dropped little by little while being stirred at temperature of 100° C. After the completion of the addition, the mixture was stirred for 10 hours, so that Michael addition reaction took place. The yield of an adduct of polyoxypropylenediamine and hydroxyethylmethacrylate in each reaction product is shown in Table 3.

TABLE 3

| Example | Molecular weight of propylenediamine | Yield of Michael Adduct |
| --- | --- | --- |
| 5 | 230 | 98% |
| 6 | 400 | 98% |
| 7 | 2000 | 98% |

EXAMPLE 8

Except for using one mol (400 g) of polyoxypropylenetriamine having molecular weight of 400 instead of one mole (230 g) of polyoxypropylenediamine having molecular weight of 230, and 3 mols (390 g) of hydroxyethylmethacrylate, the procedure of Ex. 5 was repeated. The yield of an adduct of polyoxypropylenetriamine and hydroxyethylmethacrylate in the reaction product was 98%.

REFERENCE EXAMPLES 5-8

0.02 mol of the curing agent of Examples 5-8 was put in a 500 ml round-bottom flask. Then 0.06 mol of polypropyleneglycol having a molecular weight of 2,000 was added with 0.1 mol of tolylenediisocyanate. The mixture was stirred and blended at room temperature and gel time was measured. The gel time is shown in Table 4.

Excepting for the use of 0.02 mol of polyoxypropylenetriamine (Jeffamine ® T-403: sold by Mitsui-Texaco Chemicals Co., Ltd.) in lieu of 0.02 mol of curing agent compound shown in Example 5 for comparison, the procedure of Ref. Ex. 5 was repeated. The gel time is shown in Table 4.

TABLE 4

| Reference Example | Curing agent compounds | Gel time (minute) |
| --- | --- | --- |
| 5 | Example 5 | 17 |
| 6 | Example 6 | 23 |
| 7 | Example 7 | 28 |
| 8 | Example 8 | 21 |
| Control | Polyoxypropylenetriamine (MW 400) | 15 seconds |

EXAMPLES 9-11

One mol of polyoxypropylenediamine having molecular weight shown in Table 5 was put in a 3-liter round-bottom flask. Then 2 mols (282 g) of hydroxyethyl-alpha-cyanoacrylate was dropped little by little while being stirred at temperature of 80° C. After the completion of the addition, the mixture was stirred for 10 hours, so that a Michael addition reaction took place. The yield of an adduct of polyoxypropylenediamine and hydroxyethyl-alphacyanoacrylate is shown in Table 5.

TABLE 5

| Example | Molecular weight of polyoxypropylene-diamine | Yield of Michael adduct |
| --- | --- | --- |
| 9 | 230 | 100% |
| 10 | 400 | 100% |

TABLE 5-continued

| Example | Molecular weight of polyoxypropylene-diamine | Yield of Michael adduct |
| --- | --- | --- |
| 11 | 2000 | 100% |

EXAMPLE 12

Except for the use of one mol (400 g) of polyoxypropylenetriamine instead of one mol (230 g) of polyoxypropylenediamine having molecular weight of 230, and 3 mols (423 g) of hydroxyethyl-alphacyanoacrylate ester, the procedure of Ex. 9 was repeated. The yield of an adduct of polyoxypropylenetriamine and hydroxyethyl-alphacyanoacrylate in the reaction product was 100%,

REFERENCE EXAMPLE 9-12

0.02 mol of the curing agent of Examples 9-12 was put in a 500 ml round-bottom flask. Then, 0.06 mol of polypropyleneglycol having molecular weight of 400 was added with 0.1 mol of hydrogenated diphenylmethanediisocyanate. The mixture was stirred and blended at room temperature, and gel time was measured. The gel time is shown in Table 6.

Except for the use of 0.02 mol of polyoxypropylenediamine having molecular weight of 2,000 instead of 0.02 mol of curing agent compound of Example 9 for comparison, the procedure of Ref. Ex. 9 was repeated. The gel time is shown in Table 6.

TABLE 6

| Reference Examples | Curing agent compound | Gel time (minute) |
| --- | --- | --- |
| 9 | Example 9 | 17 |
| 10 | Example 10 | 22 |
| 11 | Example 11 | 28 |
| 12 | Example 12 | 21 |
| Control 3 | Polyoxypropylenediamine (MW 2000) | 18 seconds |

EXAMPLES 13-15

One mol of polyoxypropylenediamine having the molecular weight shown in Table 7 was put in a 3-liter round-bottom flask. Then, 2 mols (320 g) of diethyleneglycolmonoacrylate was dropped little by little while being stirred at temperature of 100° C. After the completion of the addition, the mixture was further stirred for 10 hours, so that Michael addition reaction took place. The yield of an adduct of polyoxypropylenediamine and diethyleneglycolmonoacrylate in each reaction product is shown in Table 7.

TABLE 7

| Examples | Molecular weight of polyoxypropylene-diamine | Yield of Michael adduct |
| --- | --- | --- |
| 13 | 230 | 98% |
| 14 | 400 | 98% |
| 15 | 2000 | 95% |

EXAMPLE 16

Excepting the use of one mol (400 g) of polyoxypropylenetriamine instead of one mol (230 g) of polyoxypropylenediamine having molecular weight of 230 and 3 mols (480 g) of diethyleneglycolmonoacrylate ester, he procedure of Example 13 was repeated. The yield of an adduct of polyoxypropylenetriamine and diehyleneglycolmonoacrylate in the reaction product was 98%.

EXAMPLES 17–19

One mol of polyoxypropylenediamine having the molecular weight shown in table 8 was put in a 3-liter round-bottom flask. Then, 2 mols (230 g) of N-hydroxyethylacrylamide was dropped little by little while being stirred at 100° C. After the completion addition, the mixture was further stirred and blended for 10 hours, so that Michael addition reaction took place. The yield of an adduct of polyoxypropylenediamine and N-hydroxyethylacrylamide for each reaction product is shown in Table 8.

TABLE 8

| Examples | Molecular weight of polyoxypropylenediamine | Yield of Michael adduct |
|---|---|---|
| 17 | 230 | 98% |
| 18 | 400 | 98% |
| 19 | 2000 | 95% |

EXAMPLE 20

Excepting the use of one mol (400 g) of polyoxypropylenetriamine having molecular weight of 400 in lieu of one mol (230 g) of polyoxypropylenediamine having molecular weight of 230, and N-hydroxyethylacrylamide (345 g), the procedure of Example 17 was repeated. The yield of an adduct of polyoxypropylenetriamine and N-hydroxyethylacrylamide in the reaction product was 98%.

EXAMPLES 21–23

One mol of polyoxypropylenediamine having molecular weight shown in Table 9 was put in a 3-liter round-bottom flask. Then, 2 mols (318 g) of N,N-bis(hydroxyethyl) acrylamide were dropped little by little while being stirred at temperature of 100° C. After the completion of the addition, the mixture was stirred for 10 hours, so that Michael addition reaction took place. The yield of an adduct of polyoxypropylenediamine and N,N-bis(hydroxyethyl) acrylamide in each reaction product is shown in Table 9.

TABLE 9

| Examples | Molecular weight of polyoxypropylenediamine | Yield Michael adduct |
|---|---|---|
| 21 | 230 | 98% |
| 22 | 400 | 98% |
| 23 | 2000 | 90% |

REFERENCE EXAMPLES 6–7

The 0.02 mol of curing agent compounds shown in Examples 19, 23 was put in a 500 ml round-bottom flask. Then, 0.06 mol of polypropyleneglycol having molecular weight of 2,000 was added and further with 0.1 mol of tolylenediisocyanate. The mixture was stirred and blended at room temperature and gel time was measured. The results are shown in Table 10.

Except for the use of 0.02 mol of polyoxypropylenediamine having molecular weight of 2,000 in lieu of 0.02 mol of curing agent of Example 19 for comparison, the procedure of Reference Example 6 was repeated. The gel time is shown in Table 10.

TABLE 10

| Reference Examples | Curing agent compound | Gel time |
|---|---|---|
| 6 | HEAA/D 2000 (Example 19) | 35 minutes |
| 7 | BHEAA/D 2000 (Example 23) | 40 minutes |
| Control 4 | Polyoxypropylenediamine (MW 2000) | 18 seconds |

EXAMPLES 24–26

One mol of each polyoxypropylenediamine having the molecular weights shown in Table 11 was put into a 3-liter round-bottom flask. Then, 2 mols (258 g) of N-hydroxyethylmethacrylamide was added to each flask while stirring at 100° C. After completing the addition, the mixture was stirred for 10 hours and heated at 120° C., to cause a Michael addition reaction to occur. The yield of an adduct of each polyoxypropylenediamine and N-hydroxyethylmethacrylamide in each example is shown in Table 11.

TABLE 11

| Examples | Molecular weight of polyoxypropylenediamine | Yield of Michael adduct |
|---|---|---|
| 24 | 230 | 98% |
| 25 | 400 | 95% |
| 26 | 2000 | 90% |

EXAMPLES 27–29

One mol of polyoxypropylenediamine having molecular weight shown in Table 12 was put in a 3-liter round-bottom flask. Then, 2 mols (280 g) of N-hydroxyethyl-alphacyanoacrylamide was dropped little by little while being stirred at 80° C. After the completion of the addition, the mixture was further stirred for 10 hours, so that Michael addition reaction took place. The yield of an adduct of amine and N-hydroxyethyl-alphacyanoacrylamide in each reaction product is shown in Table 12.

TABLE 12

| Examples | Molecular weight of polyoxypropylenediamine | Yield of Michael adduct |
|---|---|---|
| 27 | 230 | 100% |
| 28 | 400 | 100% |
| 29 | 2000 | 98% |

EXAMPLE 30

One mol (400 g) of polyoxypropylenetriamine having molecular weight of 400 was put in a 3-liter round-bottom flask. Then, 3 mols (420 g) of N-hydroxyethyl-alphacyanoacrylamide were dropped little by little while being stirred at 80° C. After the completion of the drop, the mixture was further stirred for 10 hours, so that Michael addition reaction took place. The yield of an adduct in the reaction product was 100%.

EXAMPLE 31

Using bis (aminopropyl) polyoxyethyleneglycol ether instead of polyoxypropylenediamine, the procedure of Example 9 was repeated. The yield of adduct was 98%.

EXAMPLE 32-34

One mol of polyoxypropylenediamine having molecular weight shown in Table (13) was put in a 3-liter round-bottom flask. Then, it was heated at 140° C. under nitrogen and 3 mols of n-butylglycidylether were slowly added. After the completion of the addition, the mixture was subjected to reaction for 2 hours. Unreacted n-butylglycidylether was evaporated under reduced pressure and a polyoxypropylenediamine n-butylglycidylether adduct was obtained.

The hydroxyl value of each reaction adduct is shown in Table 13.

TABLE 13

| Examples | Polyoxypropylene (molecular weight) | Hydroxyl value of adduct (KOH mg/g) | Code |
| --- | --- | --- | --- |
| 32 | 230 | 237 | nBGE/D-230 |
| 33 | 400 | 178 | nBGE/D-400 |
| 34 | 2000 | 54 | nBGE/D-2000 |

EXAMPLE 35

Except for the use of one mol (400 g) of polyoxypropylenetriamine having molecular weight of 400 instead of one mol (2,000 g) of polyoxypropylenediamine having molecular weight of 2,000, and 4 mols (520 g) of n-butylglcidylether, the procedure of Examples 35-37 was repeated. The hydroxyl value of obtained polyoxypropylenetriamine n-butylglycidylether reaction adduct (code: nBGE/T-403) was 221 KOHmg/g.

EXAMPLE 36-38

One mol (2,280 g) of the product of Example 34 was put in a 5-liter round-bottom flask. Then, it was heated at 100° C. under nitrogen and 2.5 mols of hydroxyethylacrylate was dropped little by little. After the completion of the addition, the mixture was subjected to further reaction for 5 hours. After the end of reaction, the unreacted acrylate was evaporated under reduced pressure and the acrylate adduct was obtained. The results of each reaction product are shown in Table 14.

TABLE 14

| Examples | nBGE adduct | Functionality[1] | Average molecular weight | hydroxyl value (KOHmg/g) | Code |
| --- | --- | --- | --- | --- | --- |
| 36 | nBGE/D-230 | 4 | 720 | 310 | HEA/nBGE/D-230 |
| 37 | nBGE/D-400 | 4 | 890 | 250 | HEA/nBGE/D-400 |
| 38 | nBGE/D-2000 | 4 | 2500 | 90 | HEA/nBGE/D-2000 |

[1]Equivalent to imino or reactive hydrogen.

EXAMPLE 39

Except for the use of one mole (680 g) of BGE/T 403 obtained in Example 38 and 3.75 mols (435 g) of hydroxyethylacrylate, the procedure of Ex. 39-41 was repeated. The obtained adduct of n-BGE/T-403 and hydroxyethylacrylate (code HEA/nBGE/T-403) has a functionality of 6, a average molecular weight of 900 and a hydroxyl value of 370 KOHmg/g.

REFERENCE EXAMPLE 13

0.1 mol of the curing agents of Examples 39-42 was put in a 500-ml round-bottom flask. Then, 0.2 mol of tolylenediisocyanate was added. The mixture was stirred and blended. Time required until the mixture was geled, was measured as an indicator of reactivity with isocyanate. The results are shown in Table 15.

TABLE 15

| Reference Examples | Curing Compound | Gel time (minute) |
| --- | --- | --- |
| 13 | HEA/nBGE/D-230 (Example 39) | 15 |
| 14 | HEA/nBGE/D-400 (Example 40) | 30 |
| 15 | HEA/nBGE/D-200 (Example 41) | 35 |
| 16 | HEA/nBGE/T-403 (Example 42) | 18 |

The molar ratios forth curing compounds of table 15 were:
HEA/nBGE/D-230 (or D-400 or D-2000)=1.84/2.16/1 (molar ratio) in reaction product
HEA/nBGE/T-403=2.76/3.24/1 (molar ratio)

EXAMPLE 40

One mol (2,232 g) of Michael-type adduct of polyoxypropylenediamine having molecular weight of 2,000 and hydroxyethylacrylate obtained in Example 3 was put in a 3-liter round-bottom flask. Then, it was stirred under nitrogen and heated at 100° C. with 2.5 mol (325 g) of n-butylglycidylether were dropped little by little. After the addition, the mixture was subjected to further reaction at the same temperature for 15 hours. After completion of the reaction, unreacted n-butylglycidylether was evaporated under reduced pressure, and afterward a final product was obtained. The same procedure was carried out also with Michael-type adduct of the other polyoxypropylenediamine and hydroxyethylacrylate having different molecular weight described in the above examples.

REFERENCE EXAMPLES 14-15

0.05 mol of the curing agent compound of Example 42 was put in a 500 ml round-bottom flask and 0.1 mol of tolylenediisocyante was added. The mixture was stirred at room temperature and blended. The gel time was measured. The results are shown in Table 16. (No polyol is blended.)

TABLE 16

| Reference Examples | Curing Agent Compound | Gel time (minute) |
| --- | --- | --- |
| 14 | HEA/D-2000/n-butyglycidylether | 35 |
| 15 | (HEA/D-400/n-butylglycidylether) | (20) |

Unreacted acrylate and solvent (when used) can be removed by azeotroping. To minimize the amount of unreacted acrylate in the product, an amount of acrylate close to the theoretical should be used.

The curing agents of the invention have utility as chain extenders for flexible urethane, urethane latex and urethane encapsulation. They give the urethane product mechanical strength and elongation properties. The agents have improved solubility in polyols and improve cross-linking properties. The present curing agents are useful in the preparation in known manner of polyurethanes by the condensation reaction of a polyisocyanate and a hydroxyl-group-containing material (polyols):

$$R.NCO + R_2OH \rightarrow R.NHCOOR_2$$

Polyols with which the subject curing agents can be used include polyethyleneglycol having a molecular weight of approx. 200-600, block polymers of polyethyleneglycol and polypropyleneglycol having a molecular weight of about 400-3000, and the like.

Isocyanates with which the subject curing agents can be used include tolylenediisocyanate, liquid diphenylmethanediisocyanate, polymerized aromatic isocyanate, and the like.

The subject curing agent is used in a ratio of 5-100 and preferably, 10 to 20 weight percent, basis polyol.

What is claimed is:

1. Curing agents for polyurethane preparation comprising reaction products of (1) a polyoxyalkylene polyamine with (2) a derivative of acrylic acid or an alpha-substituted acrylic acid having a terminal hydroxyl group; or (3) a compound having an oxy ring and reaction products of (1) and (2), above, with (3) and reaction products of (1) and (3), above, with (2).

2. Curing agents of claim 1 wherein said polyamine is polyoxypropylenediamine of the formula:

$$H_2NCH(CH_3)CH_2[OCH_2CH(CH_3)]_nNH \quad (I)$$

wherein, n=2-50 a bispropylenediamine of polyoxyethylene of the formula:

$$H_2N(CH_2)_3[O(CH_2)_2]_mO(CH_2)_3NH_2 \quad (II)$$

wherein, m=1-50 or a triamine of polyoxypropylene of the formula:

$$\begin{array}{c} CH_2[OCH_2CH(CH_3)]_xNH_2 \\ | \\ CH_3CH_2C-CH_2[OCH_2CH(CH_3)]_yNH_2 \\ | \\ CH_2[OCH_2CH(CH_3)]_zNH_2 \end{array} \quad (III)$$

wherein x+y+x=3-10

3. Curing agents according to claim 2 wherein said formula I represents a compound wherein n is 2.6; 5.6 or 3.1.

4. Curing agents according to claim 2 wherein said formula II represents a compound wherein n is 2.

5. Curing agents according to claim 2 wherein said formula III represents a compound wherein x+y+z is .3.

6. Curing agents according to claim 1 wherein said acrylic acid derivative has the formula:

$$\begin{array}{c} X \\ | \\ CH_2=C-C-[Y]\underline{Z-Y-OH} \\ \parallel \\ O \end{array}$$

wherein X=H, —CH$_3$, —CN; Y=alkylene, oxyalkylene or alkyleneimine and Z is —O—, —NH—, or -N—Y—OH.

7. Curing agents according to claim 6 wherein said derivative is an acrylate, methacrylate, alphacyanoacrylate ester, N-substituted acrylamide, N-substituted methacrylamide, N-substituted- and N,N-bis-substituted alphacyanoacrylamides of hydroxyethyl, hydroxypropyl, hydroxybutyl, polyoxyethyleneglycol, polyoxypropyleneglycol and hydroxethyliminoethyl derivatives of acrylic acid.

8. Curing agents according to claim 1 wherein the ratio of polyamine to acrylic acid derivative ranges from 5:1 to 1:5.

9. Curing agents according to claim 1 wherein said compound having an oxyrane ring has the formula:

$$R'-CH\underset{O}{\overset{}{\diagdown\diagup}}CH_2$$

wherein R' is hydrogen, alkyl group, aromatic group, oxyalkyl group, or oxyalkylaromatic group.

10. Curing agents according to claim 1 wherein there is used a mol ratio of polyamine to epoxy compound of 1:1.5 to 1:5.5.

11. Curing agents according to claim 1 wherein there is used a molar ratio of reaction product of (1) and (3) with (2) of 1:1 to 1:4.

12. Curing agents according to claim 1 wherein there is used a mol ratio of reaction product of (1) and (2) with (3) ranging from 1:1 to 1:4.

13. Curing agents according to claim 1 selected from the group of the Michael reaction adducts of polyoxypropylenediamine and hydroxyethylacrylate; polyoxypropylenetriamine and hydroxyethylacrylate; polyoxypropylenediamine and hydroxyethylmethacrylate; polyoxypropylenetriamine and hydroxyethylmethacrylate; polyoxypropylenediamine and hydroxyethyl-alphacyanoacrylate; polyoxypropylenetriamine and hydroxyethyl-alphacyanoacrylate; polyoxypropylenediamine and diethyleneglycolmonoacrylate; polyoxypropylenediamine and N-hydroxyethylacrylamide; polyoxypropylenetriamine and N-hydroxyethylacrylamide; polyoxypropylenediamine and N,N-bis (hydroxyethyl) acrylamide; polyoxypropylenediamine and N-hydroxyethylmethaacrylamide; polyoxypropylenediamine and N-hydroxyethyl-alphacyanoacrylamide; polyoxypropylenetriamine and N-hydroxyethyl-alphacyanoacrylamide; bis (aminopropyl) polyoxyethyleneglycol ethers of the foregoing acrylic acid derivatives.

14. Curing agents according to claim 1 selected from the group of adducts of polyoxypropylenediamine and n-butylglycidylether; polyoxypropylenetriamine and n-butylglycidylether.

15. Curing agents according to claim 1 selected from the group of the adducts of polyoxypropylenediamine-n-butylglycidylether and hydroxyethylacrylate; polyoxy propylenetriamine-n-butylglycidylether and hydroxyethylacrylate; and polyoxypropylenediamine hydroxyethylacrylate and n-butylglycidylether.

16. Curing agents according to claim 1 containing also unreacted polyoxyalkylenepolyamine and/or unreacted acrylic acid derivative.

17. A process for preparing polyurethanes comprising condensing a polyisocyanate and a hydroxyl-containing compound in the presence of from 5 to 100 weight percent based on said compound of at least one curing agent according to claim 1.

* * * * *